United States Patent
Tanriverdi et al.

(10) Patent No.: US 12,178,724 B2
(45) Date of Patent: Dec. 31, 2024

(54) APPARATUS COMPRISING A FLEXIBLE SHEET WITH A HOLLOW CHAMBER

(71) Applicant: Unhindr LTD, London (GB)

(72) Inventors: Ugur Tanriverdi, London (GB); Firat Guder, London (GB)

(73) Assignee: Unhindr LTD, London (GB)

( * ) Notice: Subject to any disclaimer, the term of this patent is extended or adjusted under 35 U.S.C. 154(b) by 299 days.

(21) Appl. No.: 15/733,626

(22) PCT Filed: Mar. 20, 2019

(86) PCT No.: PCT/GB2019/050782
§ 371 (c)(1),
(2) Date: Sep. 18, 2020

(87) PCT Pub. No.: WO2019/180431
PCT Pub. Date: Sep. 26, 2019

(65) Prior Publication Data
US 2021/0128326 A1    May 6, 2021

(30) Foreign Application Priority Data
Mar. 20, 2018   (GB) ..................... 1804453

(51) Int. Cl.
*A61F 2/78*   (2006.01)
*A61F 2/68*   (2006.01)
(Continued)

(52) U.S. Cl.
CPC .............. *A61F 2/7843* (2013.01); *A61F 2/68* (2013.01); *A61F 2/80* (2013.01);
(Continued)

(58) Field of Classification Search
CPC .. A61F 2/7843; A61F 2/68; A61F 2/80; A61F 2002/6827; A61F 2002/704; B25J 9/16; G05B 15/02
See application file for complete search history.

(56) References Cited

U.S. PATENT DOCUMENTS

| 5,813,142 A | 9/1998 | Demon |
| 2003/0181990 A1 | 9/2003 | Phillips |

(Continued)

FOREIGN PATENT DOCUMENTS

| DE | 10 2016 107670 B3 | 10/2017 |
| WO | 94/05177 | 3/1994 |

(Continued)

OTHER PUBLICATIONS

International Application No. PCT/GB2019/050782; "International Search Report and Written Opinion"; mailed Sep. 26, 2019; 10 pgs.

*Primary Examiner* — Bruce E Snow
(74) *Attorney, Agent, or Firm* — Hall Estill Law Firm

(57) ABSTRACT

There is provided an apparatus comprising: a flexible sheet having a hollow chamber disposed within a thickness of the flexible sheet at a localised region of the flexible sheet, and an opening for transfer of a fluid between an exterior of the flexible sheet and the hollow chamber; a fluid source configured to supply a fluid to the hollow chamber via the opening to cause an increase in at least one of the surface area or the volume of the flexible sheet at the localised region; and a control circuit for controlling the fluid source; wherein the control circuit is configured to determine a control operation by identifying a category of movement of a user and/or predicting a required change in pressure in the hollow chamber; and wherein the control circuit is configured to implement the control operation by controlling the supply of fluid to or from the hollow chamber.

11 Claims, 7 Drawing Sheets

(51) Int. Cl.
  *A61F 2/80* (2006.01)
  *A61F 2/70* (2006.01)
  *A61F 2/74* (2006.01)
  *B25J 9/16* (2006.01)
  *B32B 1/08* (2006.01)
  *B32B 3/26* (2006.01)
  *G05B 15/02* (2006.01)

(52) U.S. Cl.
  CPC . *A61F 2002/6827* (2013.01); *A61F 2002/704* (2013.01); *A61F 2/74* (2021.08); *B25J 9/16* (2013.01); *B32B 1/08* (2013.01); *B32B 3/26* (2013.01); *G05B 15/02* (2013.01)

(56) References Cited

U.S. PATENT DOCUMENTS

| | | |
|---|---|---|
| 2012/0065561 A1 | 3/2012 | Ballas et al. |
| 2013/0218296 A1 | 8/2013 | Koniuk |
| 2015/0359644 A1* | 12/2015 | Sanders .................. A61F 2/80 623/34 |
| 2016/0000583 A1 | 1/2016 | Ballas et al. |
| 2018/0161182 A1* | 6/2018 | Streeter .................. A61F 5/012 |

FOREIGN PATENT DOCUMENTS

| | | |
|---|---|---|
| WO | 2014144985 A1 | 9/2014 |
| WO | 2015/100408 A1 | 7/2015 |
| WO | 2016/036846 A1 | 3/2016 |

* cited by examiner

APPARATUS COMPRISING A FLEXIBLE SHEET WITH A HOLLOW CHAMBER

This invention relates to an apparatus comprising a flexible sheet. The invention also relates to an apparatus including a liner. The invention also relates to a method for fitting a liner to a body part. The invention also relates to a use of a flexible sheet as an interface. The invention also relates to a method for forming a flexible sheet.

BACKGROUND

At an interface between two rigid surfaces, contact of the rigid surfaces can cause resultant stresses on particular regions of the rigid surfaces. This problem may be increased when there is a substantial mismatch between the shapes of the rigid surfaces. In some cases, it may be possible to design one or more of the rigid surfaces such that they have corresponding shapes.

Another possible solution is to provide a soft interface material of a shape that substantially fills the space between the two rigid surfaces. However, these solutions are not effective when one or more of the rigid surfaces changes size and/or shape with time. In such a case, the soft interface material, and therefore one or more of the rigid surfaces, may experience increased pressure. Alternatively, spaces may appear between the rigid surfaces and/or the soft interface material, which could lead to a poorer fit between the surfaces. To avoid these problems, it may be necessary to regularly replace the soft interface material. This can be undesirable and impractical if the size and/or shape of one or more of the surfaces changes frequently.

One exemplary area where such problems are faced is in the field of prosthetics. In particular, amputees may find that prosthetic limbs do not remain fitted to their residual limbs due to changes in the size and/or shape of residual limbs. After surgery, a residual limb may expand due to post-operation oedema. The oedema may last for 12-18 months, while it is desirable for amputees to wear their first prosthetics within 3-4 weeks of surgery to allow physiotherapy sessions to commence. Extending the time between surgery and physiotherapy is undesirable due to the increased muscle loss that this entails. When a shape of a prosthetic socket is tailored to the shape of an amputee's limb within 3-4 weeks of surgery, the prosthetic socket does not remain tailored to the residual limb due to changes in the size and/or shape of the residual limb. In such a situation, pressure can be unevenly distributed on the residual limb, which can cause skin problems for the amputee. Uneven pressure, shear/tension forces and sweat can traumatise the tissue of the residual limb, which can cause inflammation, ulcers and infection.

Currently, partial solutions exist that can accommodate small variations in limb shape and/or size. Prosthetic liners comprising rubber U-shaped sleeves can be fitted to the limb, with cotton socks worn between the prosthetic liner and the prosthetic socket. Changing the thickness of the cotton sock used can accommodate small changes in limb size and/or shape. However, these cotton socks can cause excess sweating by the limb, especially when multiple layers of socks are combined. When the limb gets wet, the friction between the liner and the residual limb decreases, which may cause suspension of the prosthetic and liner by the residual limb to become less effective. Such loss of suspension is important because the prosthetic limb may rely on such suspension to remain attached to the residual limb. Moreover, the use of different thicknesses of cotton socks does not mitigate changes in surface geometry, which is a critical factor in pressure distribution.

The only current option for large fluctuations in the limb's shape and/or size is to replace the socket, which may be time-consuming and expensive. In addition, in the period before a new fitted socket is made, an amputee may have to go without using a prosthetic limb, which can have effects on the amputee's standard of life and can delay rehabilitation. Even if a new socket is made, it may not fit once it has arrived due to changes in the limb's size and/or shape occurring during the time taken for the new socket to be made.

Based on the above, there is a need to provide an improved flexible interface between rigid surfaces which can accommodate differences in size and/or shape.

SUMMARY

Aspects and features of the present invention are defined in the accompanying claims.

According to a first aspect of the invention, there is provided an apparatus comprising: a flexible sheet having a hollow chamber disposed within a thickness of the flexible sheet at a localised region of the flexible sheet, and an opening for transfer of a fluid between an exterior of the flexible sheet and the hollow chamber; a fluid source configured to supply a fluid to the hollow chamber via the opening to cause an increase in at least one of the surface area or the volume of the flexible sheet at the localised region; and a control circuit for controlling the fluid source; wherein the control circuit is configured to determine a control operation by identifying a category of movement of a user and/or predicting a required change in pressure in the hollow chamber; and wherein the control circuit is configured to implement the control operation by controlling the supply of fluid, optionally via valves, to or from the hollow chamber.

Optionally, the control circuit comprises at least one electronic sensor.

Optionally, the control circuit is configured to determine the control operation based on feedback from the at least one sensor.

Optionally, the control circuit is configured to determine a control operation by identifying a category of movement by matching the feedback to a particular periodic pattern indicative of the category of movement.

Optionally, the control circuit is configured to determine a control operation by predicting a required change by matching the feedback to a particular characteristic pattern or sequence indicative of a required change based on past control operations.

Optionally, the control circuit is configured to log feedback from the at least one sensor and past control operations, and to analyse the logged feedback to determine periodic patterns indicative of a category of movement and/or characteristic patterns or sequences of control.

Optionally, the apparatus is configured to transmit logged feedback from the at least one sensor and past control operations to a remote device and to receive data regarding periodic patterns indicative of a category of movement and/or characteristic patterns or sequences of control.

Optionally, the control circuit is configured to implement the determined control operation in response to user input.

Optionally, the control circuit is configured to automatically implement the determined control operation.

Optionally, a plurality of fluid sources is configured to supply the fluid to the opening or to a plurality of openings in the flexible sheet.

Optionally, the fluid is a gas.

Optionally, the fluid source is a compressed fluid source, such as a compressed fluid canister.

Optionally, the compressed fluid source is replaceable or refillable.

Optionally, the control circuit is configured to control the supply of fluid to the hollow chamber by releasing gas from the compressed fluid source into the hollow chamber and/or to control the supply of fluid from the hollow chamber by releasing gas to the exterior of hollow chamber, and optionally to the exterior of the apparatus.

According to a second aspect of the invention, there is provided an apparatus comprising: a sheet having a hollow chamber disposed within a thickness of the sheet, and an opening for transfer of a fluid between an exterior of the sheet and the hollow chamber; a fluid source configured to supply a fluid to the hollow chamber via the opening; and a control circuit for controlling the fluid source; wherein the fluid source is a compressed fluid source.

Optionally, the sheet is a flexible sheet, the hollow chamber is disposed within the thickness of the flexible sheet at a localised region of the sheet, and the fluid source is configured to supply the fluid to the hollow chamber via the opening to cause an increase in at least one of the surface area or the volume of the flexible sheet at the localised region.

Optionally, the control circuit is configured to control the fluid source to provide a cooling effect in the flexible sheet.

Optionally, the apparatus of the first or second aspect is one of a mattress, a wheelchair, a prosthetic limb, a helmet, a ski boot, a sole for a shoe, or a medical or non-medical device arranged for skin contact.

According to a third aspect of the invention there is provided a system comprising the apparatus of the first aspect being configured to transmit logged feedback from the at least one sensor and/or past control operations to a remote device and to receive data regarding periodic patterns indicative of a category of movement and/or characteristic patterns or sequences of control, the system further comprising a device remote to that apparatus, wherein the remote device is configured to analyse the logged feedback from the at least one sensor and/or the past control operations, to determine the periodic patterns indicative of a category of movement and/or characteristic patterns or sequences of control, and to transmit data regarding the periodic patterns indicative of a category of movement and/or characteristic patterns or sequences of control to the apparatus.

According to a fourth aspect of the invention there is provided a method of controlling the inflation of a flexible sheet, the flexible sheet having a hollow chamber disposed within a thickness of the flexible sheet at a localised region of the flexible sheet, and an opening for transfer of a fluid between an exterior of the flexible sheet and the hollow chamber, the method comprising: identifying a category of movement of a user and/or predicting a required change in pressure in the hollow chamber; determining a control operation based upon the identified category of movement or predicted required change in pressure in the hollow chamber; and implementing the control operation by controlling a supply of fluid to or from the hollow chamber.

Optionally, the method further comprises determining the control operation by identifying a category of movement by matching sensor feedback to a particular periodic pattern indicative of the category of movement.

Optionally, the method further comprises determining the control operation by predicting a required change by matching sensor feedback to a particular characteristic pattern or sequence indicative of a required change based on past control operations.

Optionally, the method further comprises logging information regarding sensor feedback associated with the flexible sheet and past control operations of the flexible sheet, and analysing the logged information to determine periodic patterns indicative of a category of movement and/or characteristic patterns or sequences of control.

Optionally, the steps of identifying and determining are based on the periodic patterns indicative of a category of movement and/or characteristic patterns or sequences of control.

According to a fifth aspect of the invention, there is provided a computer program comprising code means that, when executed by a computer system, instruct the computer system to perform the method of any one of the variations of the method of the fourth aspect.

According to a sixth aspect of the invention, there is provided a computer system for controlling the inflation of a flexible sheet, the system comprising at least one processor and memory, the memory storing code that, when implemented, performs the method of any one of the variations of the method of the fourth aspect.

There is also disclosed a liner comprising: a flexible sheet with an annular cross-section along at least a portion of a longitudinal axis of the flexible sheet; a hollow chamber disposed within a thickness of the flexible sheet at a localised region of the flexible sheet; and an opening for transfer of a fluid between an exterior of the flexible sheet and the hollow chamber, wherein a transfer of the fluid to the hollow chamber causes an increase in at least one of a surface area or a volume of the flexible sheet at the localised region.

Optionally, the longitudinal axis of the flexible sheet extends between proximal and distal ends of the flexible sheet and wherein the opening is located at one of the proximal end, the distal end, or an outer surface of the flexible sheet.

Optionally, the flexible sheet has a parabolic cross-section such that the proximal end is open and the distal end is closed. Alternatively, the flexible sheet may optionally be a flat sheet that may be wrapped around an object or body part (similar to cuffs used for monitoring blood pressure). In that case, when wrapped, the sheet forms a geometry with annular cross-section and optionally parabolic longitudinal cross section.

Optionally, the transfer of the fluid between the exterior of the flexible sheet and the hollow chamber is caused by control of a fluid source.

Optionally, a transfer of the fluid from the hollow chamber causes a decrease in at least one of the surface area or the volume of the flexible sheet at the localised region.

Optionally, the liner comprises a plurality of hollow chambers at respective localised regions of the flexible sheet.

Optionally, the plurality of hollow chambers are interconnected via at least one embedded tube such that fluid can be transferred between hollow chambers of the plurality of hollow chambers.

Optionally, differing transfer of fluid between the exterior of the flexible sheet and respective hollow chambers of the plurality of hollow chambers causes differing increases and/or decreases in the at least one of the surface area or the volume of the flexible sheet at the respective localised regions.

Optionally, in use, the liner is disposed between a rigid object and a rigid socket.

Optionally, the transfer of the fluid to the hollow chamber causes an increase in friction between the flexible sheet and the body part.

Optionally, the liner is for use in cushioning a rigid object at an interface with at least one of a prosthetic device, a ski boot or a shoe lining.

Optionally, in use, the flexible sheet is able to maintain contact with a human limb.

Optionally, the increase in the at least one of the surface area or the volume is at least one of an interior surface or an exterior surface of the flexible sheet.

Optionally, the flexible sheet comprises a polymer.

There is also disclosed an apparatus comprising the liner discussed above, the apparatus comprising: a fluid source configured to supply a fluid to the hollow chamber via the opening to cause the increase in the at least one of the surface area or the volume of the flexible sheet at the localised region; and a control circuit for controlling the fluid source.

Optionally, the control circuit comprises electronic sensors and control logic for controlling the fluid source.

Optionally, the control circuit is configured to control the fluid source based on feedback from a sensor.

Optionally, the control circuit is configured to control the fluid source based on user input.

Optionally, the control circuit is configured to identify at least one of a category of movement of a user or a change in pressure patterns and to control the fluid source based at least partially on the at least one of the category of movement or the change in pressure patterns identified.

Optionally, a plurality of fluid sources is configured to supply the fluid to the opening or to a plurality of openings in the flexible sheet.

There is also disclosed a method for fitting a liner to a body part, the liner comprising a flexible sheet with an annular cross-section along at least a portion of a longitudinal axis of the flexible sheet and a hollow chamber within a thickness of the flexible sheet at a localised region of the flexible sheet, the method comprising: inserting the body part into an interior of the liner; controlling a fluid source using a control circuit; and supplying a fluid to the hollow chamber, via an opening in the flexible sheet and using the fluid source, to cause an increase in at least one of a surface area or a volume of the flexible sheet at the localised region.

Optionally, the method comprises controlling the fluid source, using the control circuit, based on feedback from a sensor.

Optionally, the method comprises controlling the fluid source, using the control circuit, based on input from a user.

Optionally, the method comprises controlling the fluid source, using the control circuit, based on input from a mobile device.

Optionally, the method comprises controlling actuation of a plurality of fluid sources to supply the fluid to a plurality of hollow chambers of the flexible sheet.

Optionally, the method comprises selectively supplying different amounts of fluid to different hollow chambers of the plurality of hollow chambers using respective fluid sources of the plurality of fluid sources.

Also disclosed is a use of a flexible sheet as an interface between an object and a rigid surface, the flexible sheet comprising a hollow chamber disposed within a thickness of the flexible sheet at a localised region of the flexible sheet and an opening for transfer of a fluid between an exterior of the flexible sheet and the hollow chamber, wherein a transfer of fluid to the hollow chamber causes an increase in at least one of a surface area or a volume of the flexible sheet at the localised region, and wherein: the object is disposed in contact with a surface of the flexible sheet; the flexible sheet is disposed in contact with the rigid surface; and a fluid source supplies the fluid to the hollow chamber via the opening to cause increased support of the object by the flexible sheet and/or to adapt to the contour of the object.

Optionally, the flexible sheet is configured to change shape and/or volume, in response to the fluid source supplying the fluid to the hollow chamber, to cause cushioning of the object.

Optionally, actuation of a plurality of fluid sources supplies the fluid to a plurality of hollow chambers via at least one embedded tube and at least one valve.

Optionally, the shape and/or volume of the flexible sheet is varied through selective actuation of different fluid sources of the plurality of fluid sources.

Optionally, the selective actuation of the different fluid sources of the plurality of fluid sources comprises actuation of a first fluid source to supply a first amount of fluid to a first hollow chamber and actuation of a second fluid source to supply a second amount of fluid to a second hollow chamber, wherein the first amount of fluid is greater than the second amount of fluid.

Optionally, the selective actuation of the different fluid sources of the plurality of fluid sources comprises actuation of a first fluid source to supply a first amount of fluid to a first hollow chamber and actuation of a second fluid source to supply a second amount of fluid to a second hollow chamber, wherein the first amount of fluid is equal to the second amount of fluid.

Optionally, the object is a body part.

Optionally, the use of the flexible sheet comprises use for at least one of a mattress, a wheelchair, a prosthetic limb, a helmet, a ski boot, a sole for a shoe, or a medical or non-medical device arranged for skin contact.

Also disclosed is a method for forming a flexible sheet, the method comprising: curing a molding material to form a cured polymer including a hollow chamber and an embedded tube; disposing the cured polymer on an inner mold; adding uncured molding material to an outer mold; inserting the inner mold into the outer mold such that the uncured molding material is in contact with the cured polymer; curing the uncured molding material in contact with the cured polymer to form the flexible sheet; and removing the inner mold and the outer mold from the flexible sheet.

Optionally, the cured polymer comprises a plurality of hollow chambers and a plurality of embedded tubes.

Optionally, the cured polymer is arranged such that fluid can be transferred between interconnected hollow chambers of the plurality of hollow chambers via embedded tubes of the plurality of embedded tubes.

Optionally, the cured polymer includes an opening for transfer of a fluid between a fluid source and the hollow chamber.

Optionally, a plurality of cured polymers are disposed on the inner mold.

Optionally, the inner mold and the outer mold are shaped such that the flexible sheet forms a domed shape closed at one end.

Optionally, the uncured molding material comprises a polymer, and wherein inserting the inner mold into the outer mold such that the uncured molding material is in contact with the cured polymer comprises disposing the cured polymer in contact with an uncured polymer.

BRIEF DESCRIPTION OF THE DRAWINGS

Embodiments will now be described, by way of example only, and with reference to the drawings in which.

In the Figures, like elements are indicated by like reference numerals throughout.

DETAILED DESCRIPTION

As discussed in the background section, changes in size and/or shape of one or more rigid surfaces can result in a mismatch in geometries of the surfaces. This can result in increased pressure at particular points of one or more of the surfaces and/or a poorer fit between the surfaces. Providing a soft interface between the rigid surfaces is ineffective where there are large changes in size of one or both of the surfaces and where there are changes in shape of one or both of the surfaces. Hence, it is desirable to provide an interface for disposing between rigid surfaces which can accommodate changes in size and/or shape.

As used herein, rigid may be used to refer to a resistance to deformation. Rigid may not be interpreted to mean that a surface or an object is entirely inflexible or unyielding. Rigid may be interpreted to refer to a resistance to deformation that is greater than that of a flexible sheet.

The objects and surfaces referred to herein refer to elements that may be disposed in contact with a flexible sheet. In some examples, the objects or surfaces may be mechanical, structural, or medical elements. In other examples, the objects or surfaces may be body parts and/or prosthetic devices. The objects or surfaces may be medical or non-medical devices which are arranged for skin contact. The terms object and surface may be used interchangeably in the discussion of the examples disclosed.

In the below, an example of a flexible sheet is presented. It will be understood that the disclosure is not limited to this specific example, but rather that different geometries of flexible sheets are within the scope of the disclosure. The flexible sheet can be any shape suitable for acting as an interface between rigid surfaces, including parabolic, annular, planar, or a combination of some or all of these geometries.

In the below, it will further be understood that the flexible sheet disclosed is not limited to use as a liner between a body part and a prosthetic, but rather is suitable for acting as an interface between any suitable objects. In some non-limiting examples, the flexible sheet can be used to provide cushioning in a ski boot, on a wheelchair, on a mattress, or in a helmet.

Figure 1:
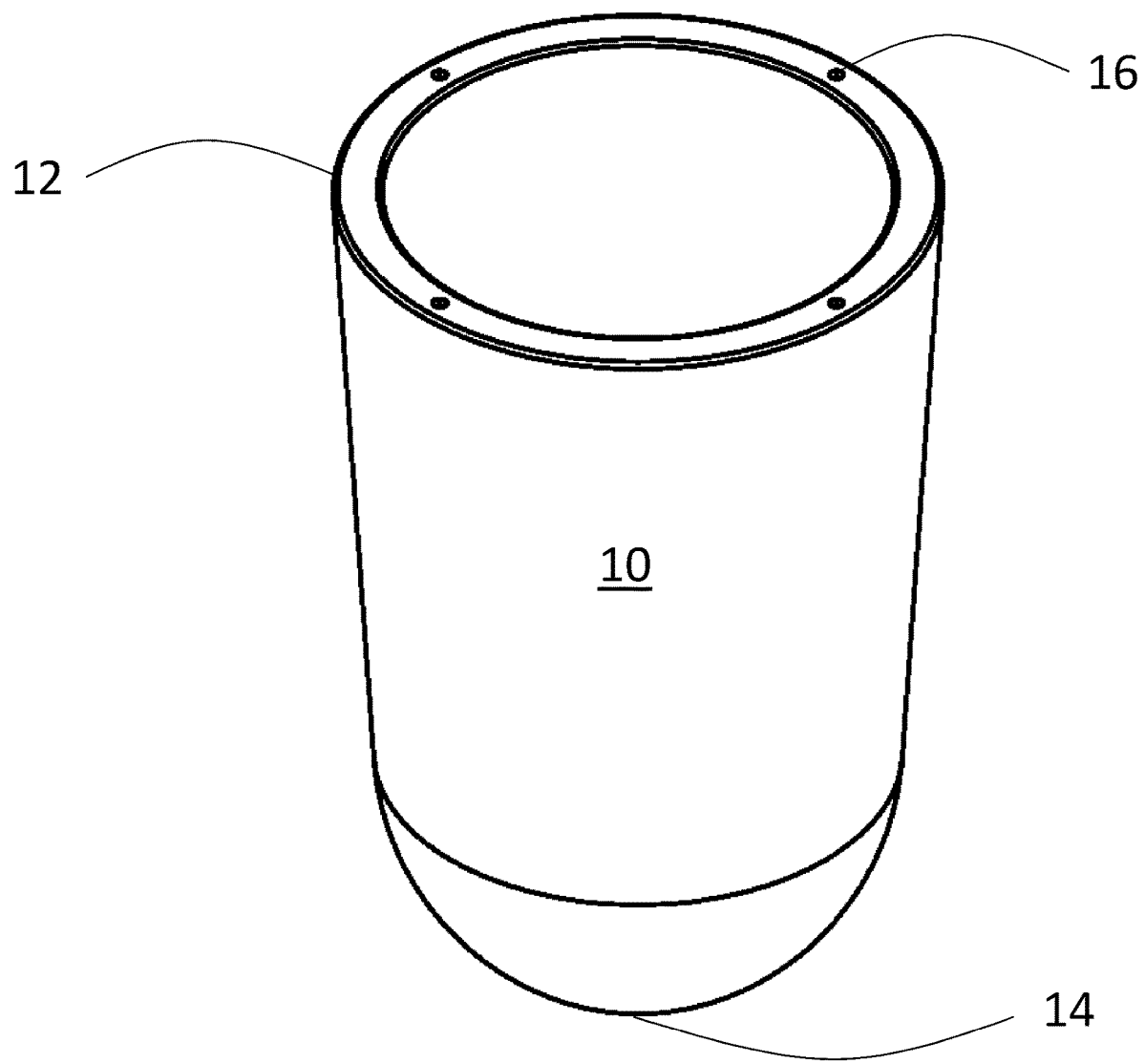
FIG. 1 illustrates an example of a flexible sheet.

Turning to FIG. 1, an example of a flexible sheet 10 is disclosed. A longitudinal axis of the flexible sheet 10 may extend from a proximal end 12 of the flexible sheet 10 to a distal end 14 of the flexible sheet 10. The flexible sheet 10 may have an annular cross-section along at least a portion of the longitudinal axis of the flexible sheet 10, in particular examples such as liners for prosthetic limbs. However, although that is how the invention is illustrated herein, it can be employed more widely for other uses in which the geometry may be different than described above, as discussed later. In the example shown in FIG. 1, the distal end 14 of the flexible sheet it closed to form a parabolic or dome-shaped flexible sheet 10. However, in some examples, the distal end 14 may be open such that the flexible sheet 10 has an annular cross-section along its entire extent. In some examples, the diameter of the area enclosed by the flexible sheet 10 may vary along the longitudinal extent of the flexible sheet. As explained above, in some examples the flexible sheet 10 may be planar (flat). In these examples, the flexible sheet 10 may support a load resting thereon, for example for use for a mattress, a sole for a shoe, or a wheelchair.

The flexible sheet 10 is suitable for use as a liner. In other words, the flexible sheet may be disposed adjacent to or between one or more rigid surfaces in order to provide support and/or cushioning. The flexible sheet 10 may consist of or comprise a polymer, such as an elastomer. This may enable the flexible sheet to maintain contact with a rigid surface when it is subject to a force acting to separate the flexible sheet and the rigid surface. In these examples, the rigid surface may be inserted into an area enclosed by the flexible sheet 10 on one or more sides.

The flexible sheet 10 includes at least one opening 16. Fluid may pass between an exterior of the flexible sheet 10 and an interior of the flexible sheet 10 via the opening 16. In the example shown in FIG. 1, the flexible sheet 10 has four openings. However, it will be understood that the flexible sheet 10 may include one, two, three, or any other suitable number of openings.

In the example shown in FIG. 1, the openings of the flexible sheet 10 are disposed at the proximal end 12 of the flexible sheet 10. However, it will be understood that the openings can be disposed at the distal end of the flexible sheet 10 or on the exterior or interior surface of the flexible sheet 10, or at any combination of these locations.

Figure 2:
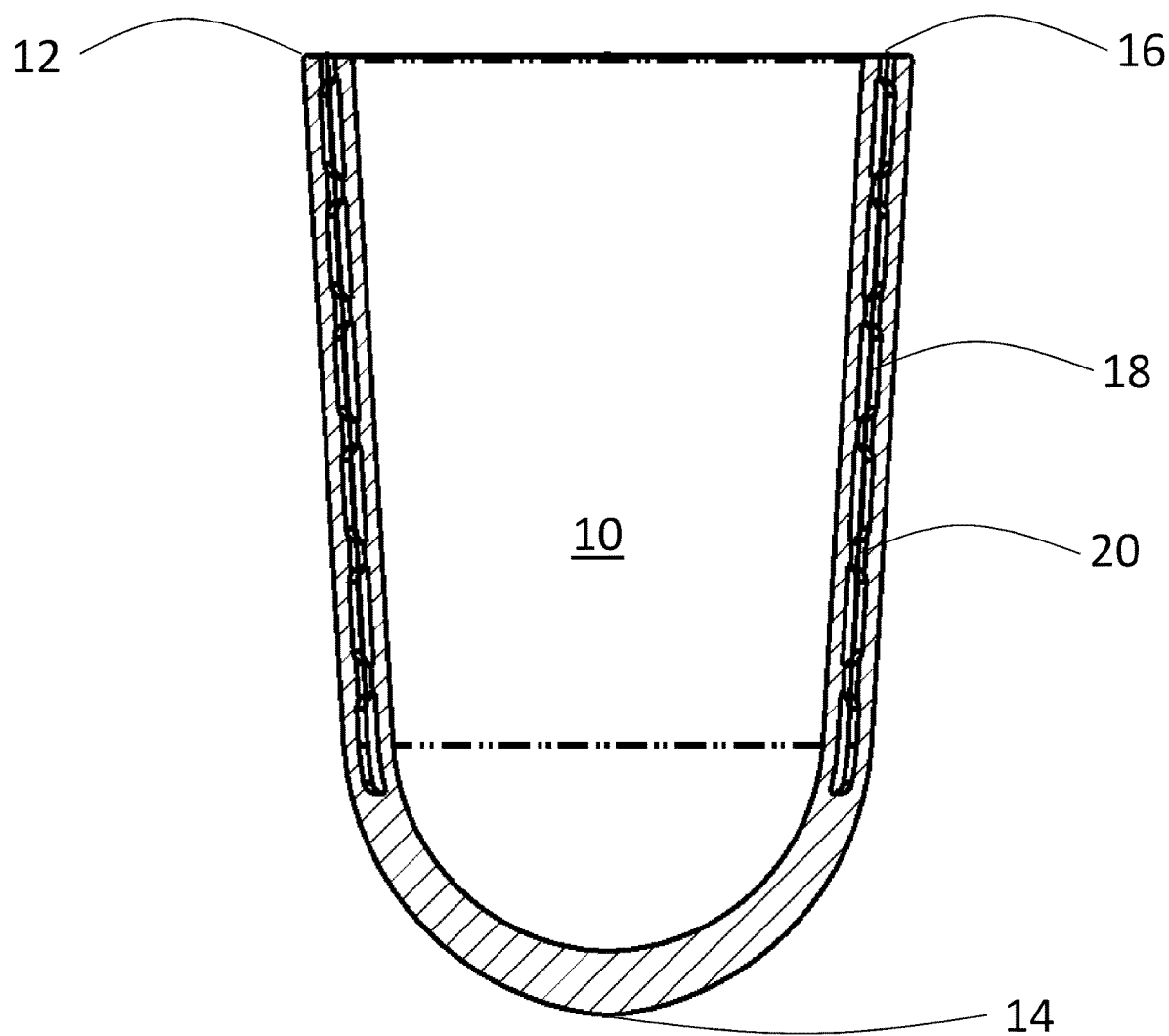
FIG. 2 illustrates a section view of an example flexible sheet.

FIG. 2 shows a section view of the flexible sheet 10. In other words, FIG. 2 shows a slice of the flexible sheet 10 taken along its longitudinal axis. The flexible sheet 10 contains at least one hollow chamber 18. The hollow chamber 18 is disposed within the thickness of the flexible sheet 10. The hollow chamber 18 is at a localised region of the flexible sheet 10. In other words, the hollow chamber 18 does not occupy the entirety or substantially the entirety of the interior of the flexible sheet 10.

In some examples, the flexible sheet 10 may contain a plurality of hollow chambers 18. Where there is more than one hollow chamber 18, one or more of the hollow chambers 18 may be connected to one or more of the other hollow chambers 18 via an embedded tube 20. An embedded tube 20 can additionally or alternatively connect a hollow chamber 18 to an opening 16. In the example shown in FIG. 2, a series of six interconnected hollow chambers 18 are linked by a corresponding series of embedded tubes 20. The hollow chamber 18 closest to the proximal end 12 of the flexible sheet 10 is connected to the opening 16 via an uppermost one of the embedded tubes 20. The opening 16 connects the uppermost one of the embedded tubes 20 to an exterior of the flexible sheet 10.

In the example shown in FIG. 2, twelve hollow chambers 18 are visible in two independent series of six interconnected hollow chambers 18. However, any number of series of any number of interconnected hollow chambers 18 may be used. In some examples, a single series of interconnected hollow chambers 18 may be used. In other examples, three, four, or any other suitable number of series of interconnected hollow chambers 18 may be used.

Where there are multiple series of interconnected hollow chambers 18, each series may be separated by a constant angle around a perimeter of the flexible sheet 10. Using a constant angle may provide an appropriate distribution of support and cushioning around an entirety of the flexible sheet 10 and a corresponding surface. In other examples, the series may be separated by differing angles. Using differing angles may be useful where there are areas where particular protrusions or pressure points are present and/or where high concentrations of hollow chambers 18 are desirable. These areas may correspond to areas where a shape and/or size of a rigid surface is expected to change by a larger amount than in other areas.

In other examples, the hollow chamber 18 may not be distributed in interconnected series extending along a linear extent of the flexible sheet 10. Each hollow chamber 18 may be independent of other hollow chambers 18. In some examples, hollow chambers 18 may be interconnected by embedded tubes 20 extending in a direction around a cross-section of the flexible sheet 10, or at an angle between the longitudinal direction and the direction around a cross-section of the flexible sheet 10.

In some examples, a single opening 16 may be used. In these examples, all of the hollow chambers 18 may be interconnected via embedded tubes 20. The hollow chambers 18 may comprise a single series of interconnected hollow chambers 18 connected to a single opening 16.

While the example shown depicts embedded tubes 20 that linearly link one hollow chamber 18 to another hollow chamber 18 (or opening 16), the embedded tubes 20 may contain any number of branches to any number of hollow chambers 18 or openings 16. For example, multiple branches in embedded tubes 20 may be used to connect more hollow chambers 18 to fewer openings 16 via a smaller number of interconnected hollow chambers 18 and embedded tubes 20.

Figure 3:
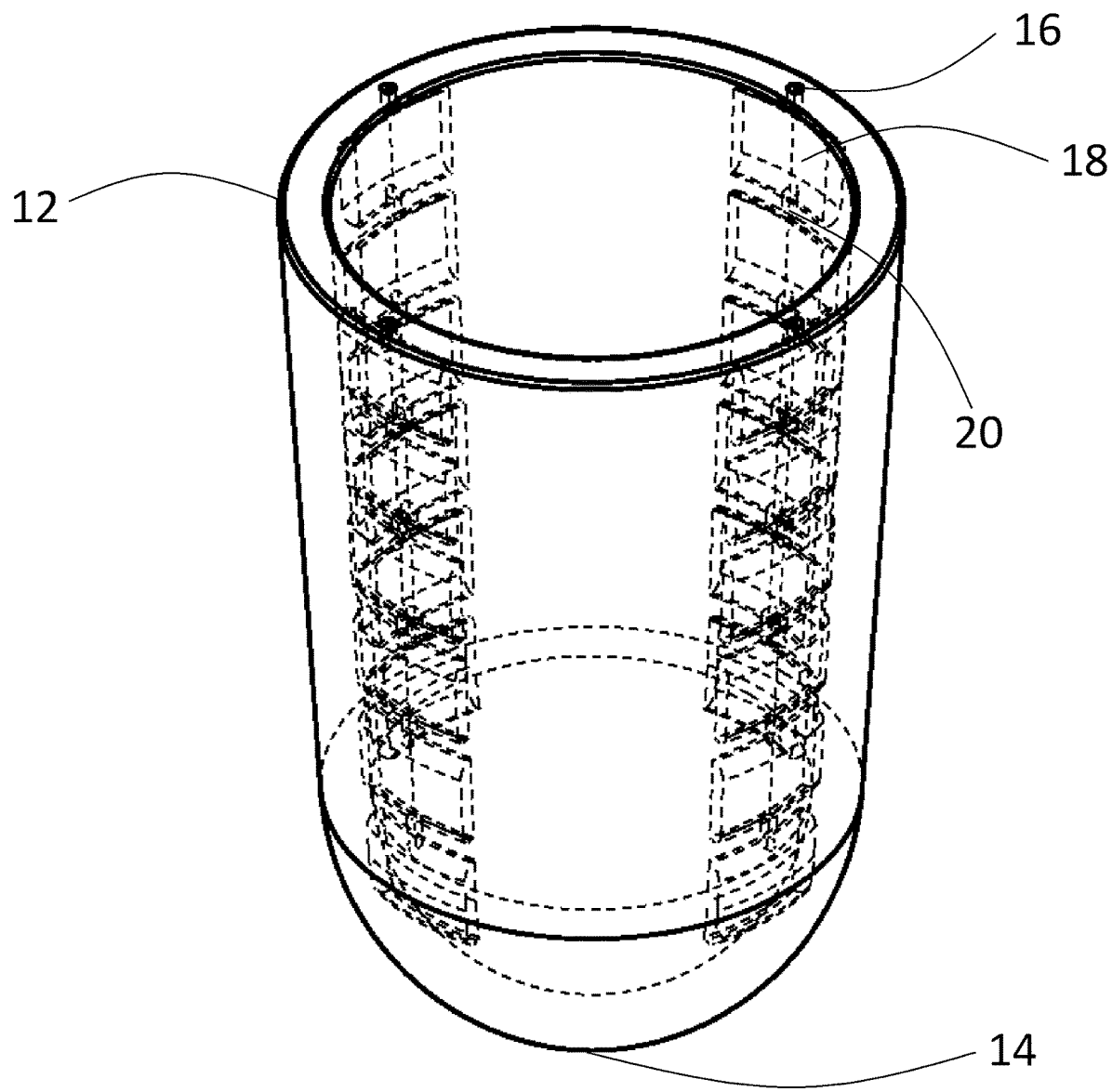
FIG. 3 illustrates a 3-D view of an example flexible sheet.

FIG. 3 shows a 3-D view of the flexible sheet 10, with dashed lines indicating the hollow chambers 18 and embedded tubes 20 disposed within the thickness of the flexible sheet 10. In the example shown in FIG. 3, there are four series of interconnected hollow chambers 18 disposed at 90° angles around a cross-section of the flexible sheet 10. In the example shown, the hollow chambers 18 are substantially cuboid in shape. However, it will be understood that any suitable shape or shapes of hollow chamber 18 can be used, such as ovoid or spherical hollow chambers 18.

The shape and/or size of a hollow chamber 18 at a particular localised region of the flexible sheet 10 may be selected to provide a specific distribution of cushioning and/or support corresponding to a particular shape of a rigid object disposed adjacent to the localised region. In the example shown in FIG. 3, the hollow chambers 18 are substantially the same size and substantially the same shape. However, in some examples, the hollow chambers 18 may be different sizes. Alternatively, or in addition, the hollow chambers 18 may be different shapes.

In the above, example flexible sheets 10 have been disclosed. These flexible sheets 10 are configured to enable fluid to be supplied to the one or more hollow chambers 18. Examples describing this fluid supply are set out below.

Figure 4:
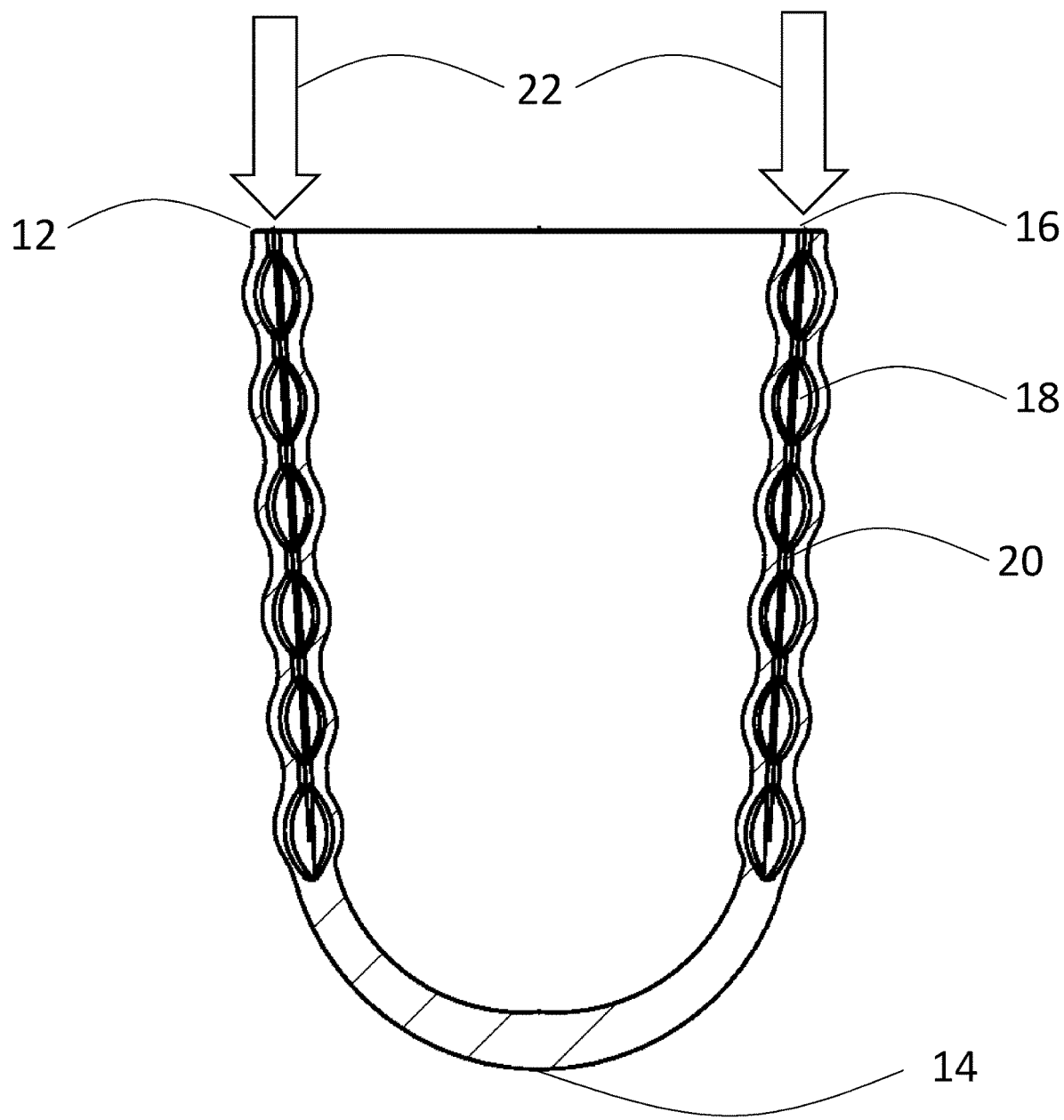
FIG. 4 illustrates a section view of an example flexible sheet with fluid supplied to the flexible chambers.

FIG. 4 shows a section view of a flexible sheet 10 with fluid supplied to the hollow chambers 18. Fluid is supplied to the one or more hollow chambers 18 via the one or more openings 16 and via one or more embedded tubes 20. The one or more openings 16 are configured to transport fluid from one or more fluid sources 22 to the one or more embedded tubes 20 and the one or more hollow chambers 18. In the example shown in FIG. 4, there is one fluid source 22 for each opening 16. However, it will be understood that one fluid source 22 can supply multiple openings 16 and/or that multiple fluid sources 22 can supply one opening 16.

The fluid source 22 can be any device suitable for supplying fluid. In some examples, the fluid source 22 may be an actuator such as a syringe or a pressurised reservoir such as a canister. In other examples, the fluid source 22 may be a disposable or refillable canister, or a fluid supply cartridge. Either of these fluid sources may be connected via an air-tight lock mechanism to tubes connecting to openings 16.

When a fluid source 22 supplies the fluid to an opening, a hollow chamber 18 may be partially or entirely filled with the fluid. If the fluid is a gas, the fluid may fill an entire volume of the hollow chamber 18. When the fluid is supplied, the hollow chamber 18 may increase in volume. The increase in volume of the hollow chamber 18 may cause an increase in surface area and/or volume of the flexible sheet 10 at the localised region of the flexible sheet 10 corresponding to the hollow chamber 18. This increase in volume may be at an interior surface of the flexible sheet 10 and/or at an exterior surface of the flexible sheet 10. In some examples, the hollow chamber 18, when filled with fluid, may extend beyond the thickness of the flexible sheet 10. The increase in volume and/or surface area is caused by increased pressure within the hollow chamber 18 caused by the supply of fluid from the fluid source 22. Hence, it is apparent that the increase in surface area and/or volume of the flexible sheet 10 at a localised region of the hollow chamber 18 is controllable by varying the fluid supplied to the hollow chamber by the fluid source 22.

Where hollow chambers 18 are interconnected by embedded tubes 20, different hollow chambers 18 may receive differing amounts of fluid and thereby be at different pressures. Alternatively, or in addition, different fluid sources 22 can be configured to supply different amounts of fluid to different openings 16 and thereby to different hollow chambers 18. The differing amounts of fluid supplied to each hollow chamber 18 can cause differing increases in surface area and/or volume at the various respective localised regions of the flexible sheet 10 corresponding to each hollow chamber 18. By these means, the thickness of the flexible sheet 10 can be varied at specific localised regions and at different times.

In some examples, the fluid may be a gas, such as air or carbon dioxide. In these examples, the fluid is a compressible fluid. In these examples, the flexible sheet 10 may be more flexible to changes in shape and/or size of an adjacent rigid surface than if a liquid were used. The gas may be supplied by a reservoir of compressed fluid, such as a compressed fluid cylinder or canister. As such, the fluid may change the shape and/or size of an adjacent rigid surface of flexible sheet 10 by using the released energy caused by de-compression of the fluid. In examples where the flexible sheet 10 is part of a larger apparatus (e.g. a prosthetic limb) the reservoir can be attached or supported on the apparatus. This is particularly convenient, for example, when considering a prosthetic limb, the flexible sheet 10 may be part of a liner inside a socket and a compressed fluid canister may be provided on the outside of the prosthetic, connected to the liner by a tube for example.

Using a compressed fluid reservoir also has the advantage that control of the filling of flexible sheet 10 may be achieved by simply opening and closing, by the control circuit, a valve or set of valves connecting the reservoir and the flexible sheet 10. That is, the pressure in the compressed fluid reservoir can cause the gas to flow into the flexible sheet 10, and if the pressure in the flexible sheet needs to be reduced, the gas can simply be released to the surrounding air or alternatively into another collecting canister. The release of the energy due to the decompression of the pressurised gas transports the fluid within the embedded tubes 20 and hollow chamber 18, and can therefore eliminate the need for a powered transport system, such as a pump or a motor supplying and/or circulating the compressible fluid within the flexible sheet 10. The elimination of such motor or pump, therefore, leads to an improved design which may be lighter and/or more silent, as well as having a lower power consumption. In that scenario, when the reservoir is spent, the reservoir can be detached and replaced. In other words, the reservoirs can be replaceable, refillable, and/or disposable.

Another advantage of using a compressible fluid is that it minimises the weight of the flexible sheet 10 and the reservoir (e.g. compared to using a liquid). Again, this is of particular advantage when considering a use case such as a prosthetic, where additional weight is undesirable. Therefore, in those uses, compressed gas provides the double advantage of reduced weight in terms of the fluid itself as well as reduced weight due to the lack of need for additional pumps/motors etc. to transfer the fluid from the reservoir to the flexible sheet 10.

A further advantage of using a compressible fluid is that decompression of the fluid results in a drop in the temperature of the released gas which may be employed to cool the object in contact with the flexible sheet 10. The gas may be circulated within the embedded tubes 20 and hollow chamber 18 of flexible sheet 10 by the control circuit receiving data from electronic sensors such as flow meters, temperature sensors, and pressure sensors that are explained later. The controlled circulation of the cooler gas within the flexible sheet 10 may not result in an increase in surface area and/or volume of the flexible sheet 10 at the localised region of the hollow chamber 18, but may only affect the temperature of the flexible sheet 10.

In other examples, the fluid may be a liquid. In these examples, the fluid may be an incompressible fluid. In these examples, the flexible sheet 10 may be more resistant to changes in shape and/or size of an adjacent rigid surface than if a gas were used. It will be understood that different kinds of fluids can be supplied to different openings 16 of the flexible sheet 10. For example, while a first fluid source may supply a gas to a first opening, a second fluid source may supply a liquid to a second opening. The first fluid and the second fluid may be selected based on the surface geometry of one or more adjacent rigid surfaces and/or a distribution of hollow chambers 18 and embedded tubes 20 disposed within the flexible sheet 10.

The arrangement of FIG. 4 is thus configured to enable the flexible sheet 10 to change in size and/or shape in response to at least one of the supply of fluid from one or more fluid sources 22, the distribution of hollow chambers 18 within the flexible sheet 10, the interconnections of hollow chambers by embedded tubes 20, and the type of fluid supplied to each opening 16. These parameters can be selected so as to achieve a desired size and/or shape of the flexible sheet 10. In particular, these parameters can be selected so as to configure a flexible sheet 10 to have a size and/or shape corresponding to a rigid surface, multiple rigid surfaces, or a space between multiple rigid surfaces. This can provide improved cushioning and/or support to the one or more rigid surfaces.

Figure 5:
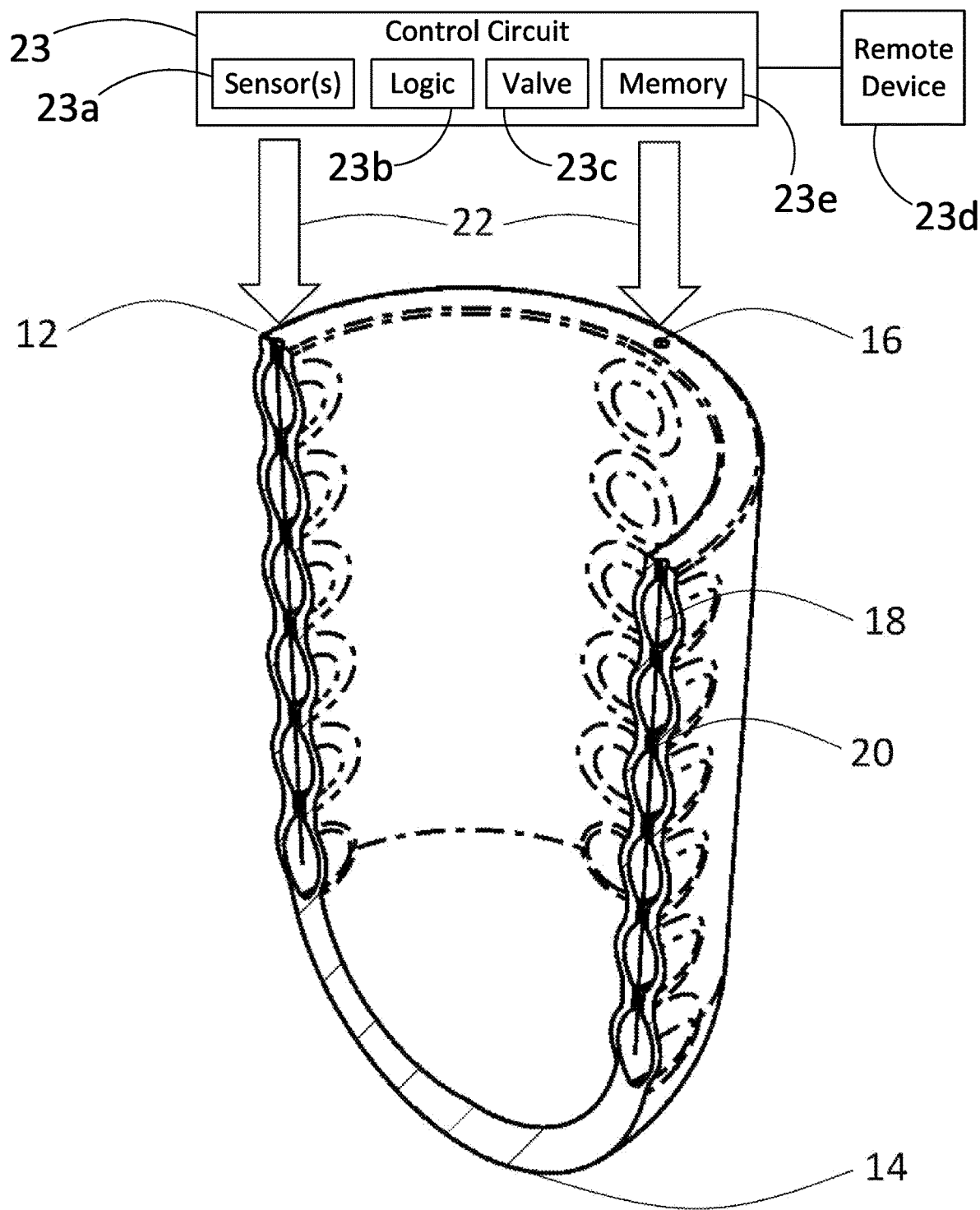
FIG. 5 illustrates a 3-D view of an example flexible sheet with fluid supplied to the flexible chambers.

FIG. 5 shows a 3-D view of a flexible sheet 10 with fluid supplied to the flexible chambers. While there are three series of interconnected hollow chambers 18 shown, it will be understood that other arrangements are possible. The distribution of fluid-filled hollow chambers 18 in 3-D around the flexible sheet demonstrates the ability to provide support to a rigid object in three dimensions. In particular, it is possible to provide support and cushioning that varies both spatially and temporally using the devices and techniques described herein.

In use, the flexible sheet 10 can be configured to conform to a current size and/or shape of one or more rigid surfaces. In use, the flexible sheet 10 can provide an interface between multiple rigid surfaces and/or can conform to a single rigid surface. In a use of the flexible sheet, an increase in pressure within a hollow chamber 18, caused by an increase in supplied fluid, can cause an increase in surface area and/or volume of the flexible sheet 10 at the localised region of the hollow chamber 18. This can cause an increase in pressure and/or an increase in friction between the flexible sheet 10 and the one or more rigid surfaces at the localised region. This friction provides an effective force opposing a force acting to separate the flexible sheet 10 and the one or more rigid surfaces. Therefore, the flexible sheet 10 can more effectively adhere to or support the one or more rigid surfaces.

As described above, parameters that may be controlled to vary the size and/or shape of the flexible sheet 10 include the supply of fluid from one or more fluid sources 22, the distribution of hollow chambers 18 within the flexible sheet 10, the interconnections of hollow chambers by embedded tubes 20, and the type of fluid supplied to each opening 16. One or more of these parameters can be varied in response to a change in size and/or shape of one or more rigid surfaces. In particular, varying one or more of the parameters during use of the flexible sheet 10 can cause the flexible sheet 10 to fit more closely to one or more rigid surfaces, even if the geometry of one or more of the rigid surfaces changes over time.

For example, a decrease in size of a rigid surface adjacent to the flexible sheet 10 can cause a decrease in pressure within the flexible sheet 10 relative to that resulting from the fluid supplied by a fluid source 22. This can be sensed by a sensor disposed between an opening 16 and the fluid source 22. In response, the fluid source 22 may increase the supply of fluid to the hollow chamber 18 so as to increase the surface area and/or volume of the flexible sheet 10 at the localised region of the hollow chamber 18. This may cause the altered size and/or shape of the one or more rigid surfaces to be better supported by the flexible sheet 10 using the increased surface area and/or volume of the flexible sheet 10 at the localised region of the hollow chamber 18.

Alternatively, or in addition, the one or more of the rigid surfaces may increase in size. This may cause an increase in pressure within the flexible sheet 10 beyond that resulting from the supply of fluid by the fluid source 22. In response, the fluid source may be configured to reduce a supply of fluid to the hollow chamber 18 and/or to effect a pressure change so as to extract fluid from the hollow chamber 18 so as to decrease the surface area and/or volume of the flexible sheet 10 at the localised region of the hollow chamber 18. This may cause the altered size and/or shape of the rigid surface to be better supported by the flexible sheet 10 using the decreased surface area and/or volume of the flexible sheet 10 at the localised region of the hollow chamber 18.

The supply of fluid by a fluid source 22 can be controlled in various ways. A control circuit 23 can be used to control the fluid source 22. The control circuit 23 may comprise electronic sensors 23a and control logic 23b for controlling the fluid source 22. In some examples, the control circuit 23 is configured to control the fluid source based on feedback from a sensor. For example, if a low pressure is sensed by a pressure sensor, the control logic 23b may control the fluid source 22 to increase a supply of fluid to the flexible sheet 10. If a high pressure is sensed by the pressure sensor, the control circuit may control the fluid source 22 to decrease a supply of fluid to the flexible sheet 10 and/or to extract fluid from the flexible sheet 10. As explained later, sensors other than pressure sensors (e.g. accelerometers, temperature sensors, flow meters, flow sensors, gyroscope sensors, GPS sensors or a clock) may be used to effect control based on a user's activity. In some examples, the control circuit 23 may control the fluid source 22 using a valve 23c (or a plurality of valves). The fluid may be extracted from the flexible sheet 10 to a reservoir and/or to the outside environment using a valve or a plurality of valves. In addition, or alternatively, one or more valves may be disposed in one or more embedded tubes 20 for controlling fluid flow between one or more openings 16 and/or one or more hollow chambers 18. In addition, or alternatively, the control circuit may be configured to control the fluid source based on input from a user. In further examples, the control circuit is configured to control the fluid source 22 based on input from a remote device 23d, such as a mobile device. For example, a user may control the fluid source 22 using an application installed on a mobile device. Combinations of these control means can be used. This may optimize control of the fluid source 22 and/or enable differing control means to be applied at different times.

Data relating to the control of one or more fluid sources 22 by the control logic 23 can be logged in a data store (memory 23e). The data store 23e and the control logic 23b can be used to identify characteristic patterns and/or sequences in the data. For example, the data may show that a particular average amount of fluid is supplied by the one or more fluid sources at night. This is an example of a pattern of control that is linked to a user's routine or schedule. Such a pattern of pressure changes and control that may be pre-emptively identified. Alternatively, the data may show that a particular periodic pattern of fluid supply occurs during a particular movement, such as walking or cycling. These are examples of patterns of control linked to a particular activity. User analysis and/or machine learning techniques may be used to develop policies that can identify a current category of movement of a user of the flexible sheet or of an object that the flexible sheet is applied in contact with, as that movement is occurring, or to predict that a particular control will be required based on a user's routine or schedule. The one or more fluid sources 22 may use the identified category of movement and/or the predicted routine to pre-emptively adjust the fluid supply based on the logged data and the identified category of movement and/or predicted routine. A user, with or without the use of a mobile device, may override the pre-emptive fluid supply as appropriate. The logic may also analyse the user's overriding commands and manual inputs, entered either via a mobile device or hardware buttons directly integrated to the apparatus associated with the flexible sheet, to further learn the user's personal preferences and to control the fluid sources 22 in regard to the optimum personalised performance.

In other words, by logging data from sensors associated with the apparatus incorporating the flexible sheet, and also data regarding past control operations, information about a user's routine habits and preferences can be determined. Those habits may relate to how the user sets the pressures for a particular type of activity, but may also relate to when particular activities occur or how pressures are set at different times of day. Such information can be derived from pressure sensors associated with the flexible sheet 10 but also other types of sensors too. For example, using GPS information allows it to be determined that particular activities/control strategies are employed in particular locations (e.g. in a park compared to at home); or using temperature sensors allows it to be determined how control strategies are altered with the weather and/or fluid temperature within the flexible sheet 10; or using accelerometers allows more precise differentiation of different types of movement; or using a clock allows a control strategy based on a user's daily routine to be determined. Alternatively and/or additionally, a flow meter or flow sensor may measure the flow rate of the fluid to control the duration of the increment in a surface area and/or volume of the flexible sheet 10. Similar to the sensor feedback above, these readings may be used to analyse the logged data and/or may be used in deriving the information about a user's routine habits and preferences.

Of course, all this information may be used together, e.g. through machine learning methods, to create policies that can form the basis for a control strategy that is both responsive and predictive based on current sensor feedback and past control inputs. That is, the control circuit may read the logged data of user movement to match the data with the corresponding periodic patterns in the pressure change history. By combining the machine-learning techniques with at least one of user's limb movement, manual overrides or previous pressure characteristics and patterns, an artificially intelligent control mechanism is achieved to control the fluid supply to the flexible sheet 10.

That system can then pre-emptively implement or suggest (e.g. by providing a notification to the user, either through the apparatus itself or a user's mobile device) such control according a user's preference. Such analysis may be implemented by the apparatus incorporating the flexible sheet 10, or may be done remotely. That is, the apparatus may have a control circuit configured to log feedback from the sensors and past control operations, and to determine the periodic patterns indicative of a category of movement and/or characteristic patterns or sequences of control, and to subsequently base control on those determined patterns. Alternatively, the apparatus may be configured to transmit logged feedback from the at least one sensor and past control operations to another device, such as a mobile device or cloud computer or server. That further device may then perform the analysis to determine the periodic patterns indicative of a category of movement and/or characteristic patterns or sequences of control. Data regarding those patterns may then be sent back to the device incorporating the flexible sheet, which may then subsequently base control on those determined patterns. In either case, it is preferable that the control and matching of sensor feedback to previously determined patterns is performed on the device, to ensure continuing operation if communication with external devices is interrupted. However, there may be some scenarios in which the matching may also be implemented remotely.

In use, supplying fluid to a hollow chamber 18 by the fluid source 22 may cause an increase in support of an object by the flexible sheet 10. Alternatively, or in addition, supplying fluid to the hollow chamber 18 by the fluid source 22 may cause an increase in friction between the flexible sheet and the object.

While the above example uses of a flexible sheet have been described in relation to one or more rigid surfaces, it will be understood that the flexible sheet is suitable for use with a variety of one or more objects or surfaces. While the figures illustrate an example of the flexible sheet with a parabolic cross-section, it will be understood that other geometries of flexible sheet are possible.

The disclosed examples include a use of a flexible sheet to substantially annularly surround an object. In addition, the disclosed examples include a use of a flexible sheet to support or cushion one or more sides of an object. For example, in use, the flexible sheet can be used as part of or in combination with a mattress to provide improved support or cushioning of an object on the mattress and/or flexible sheet. In these examples, the object can be a body part. In use, the flexible sheet can be used as part of or in combination with a shoe or a sock to improve a fitting of the shoe or sock to a foot and/or leg of a user. In another example, in use, the flexible sheet can maintain contact with a residual limb in order to suspend a prosthetic from the residual limb and to provide increased support to the residual limb.

In these examples, supplying fluid to a hollow chamber 18 of the flexible sheet 10 in use of the flexible sheet 10 can cause at least one of improved support, improved cushioning, increased friction and greater adhesion to an object disposed in contact with the flexible sheet 10.

Figure 6:
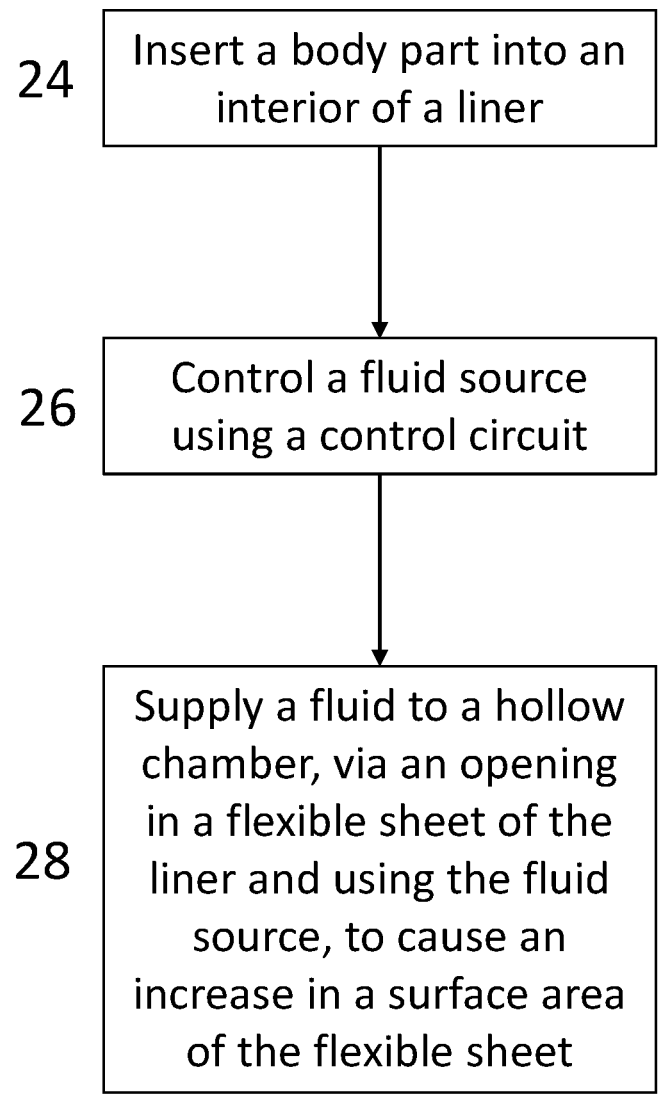
FIG. 6 illustrates a method for fitting a liner to a body part.

FIG. 6 shows a method for fitting a liner to a body part. The liner can comprise a flexible sheet 10 as described in any of the examples set out herein. The liner can comprise a flexible sheet 10 with an annular cross-section along at least a portion of a longitudinal axis of the flexible sheet and a hollow chamber 18 within a thickness of the flexible sheet 10 at a localised region of the flexible sheet 10.

In a step 24, the method may comprise inserting a body part into an interior of a liner. The body part can be a limb such as a leg or an arm, a head, or any other body part that a liner or a flexible sheet 10 as described herein is suitable for use with. The interior of the liner may comprise an area within the perimeter defined by the annular cross-section of the flexible sheet 10 of the liner.

In a step 26, a fluid source 22 can be controlled using a control circuit. The control circuit may comprise one or more electronic sensors and control logic as described herein. The control of the fluid source 22 can be based on at least one of feedback from a sensor, user input, and input from a mobile device. It can also incorporate the AI/machine learning techniques discussed above to provide personalised and predictive control. In some examples, the feedback from the user input can be via built-in hardware components.

In a step 28, a fluid can be supplied to a hollow chamber 18, via an opening in a flexible sheet 10 of the liner and using the fluid source 22, to cause an increase in a surface area and/or volume of the flexible sheet 10. As described herein, the increase in the surface area and/or volume can be at a localised region of the flexible sheet 10 corresponding to the hollow chamber 18.

While the method set out in FIG. 6 is presented in a certain sequential order, this should not be taken to limit the method to the order presented. In some examples, the fluid source 22 can be controlled and/or the fluid can be supplied to the hollow chamber 18 before insertion of a body part into the interior of the liner.

Further, while a single fluid source 22, hollow chamber 18 and opening 16 have been referred to in relation to FIG. 6  for ease of explanation, it will be apparent from discussion throughout this disclosure that multiple of these elements can be used in combination with the method of FIG. 6.

Figure 7:
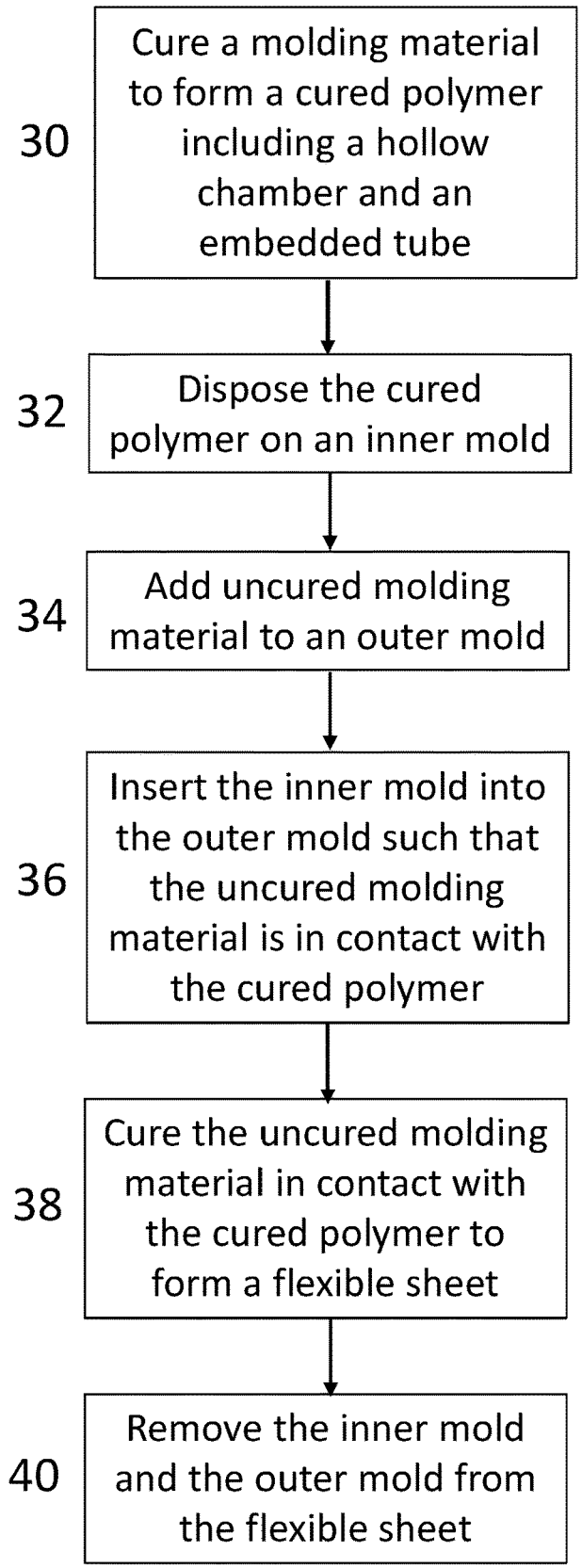
FIG. 7 illustrates a method for forming a flexible sheet.

FIG. 7 shows a method for forming a flexible sheet 10. The flexible sheet 10 can be the flexible sheet 10 described in any of the examples set out herein. The flexible sheet 10 may have an annular cross-section along at least a portion of a longitudinal axis of the flexible sheet and a hollow chamber 18 within a thickness of the flexible sheet 10 at a localised region of the flexible sheet 10. In other examples, the flexible sheet 10 can be planar or substantially planar. In other examples, the flexible sheet 10 can have a parabolic shape. The flexible sheet 10 can comprise a combination of the geometries described above.

In a step 30, a molding material can be cured to form a cured polymer including a hollow chamber 18 and an embedded tube 20. As disclosed herein, multiple hollow chambers 18 and/or multiple embedded tubes 20 may be used. The molding material may be cured around a 3-D printed mold to form the cured polymer including the hollow chamber 18 and the embedded tube 20. An additional layer of cured polymer may be adhered to the cured polymer in order to form an enclosed hollow chamber and embedded tube. The cured polymer may be configured such that an embedded tube extends to an opening 16 to an exterior of the cured polymer.

In some examples, the edges and/or corners of the 3-D printed mold may be rounded to prevent sticking (i.e. to enable easier de-molding). The 3-D printed mold may be coated with mold-release agent in order to reduce surface tension. The molding material may be degassed prior to curing.

In a step 32, the cured polymer may be disposed on an inner mold. The inner mold may be rigid and/or stiff. The inner mold may be formed using 3-D printing. The inner mold may be substantially a similar shape to a shape of flexible sheet 10 that it is desired to form. The cured polymer may be disposed on the inner mold such that an opening of the cured polymer is disposed at an extremity of the inner mold, such as at a proximal or distal end of the inner mold. In some examples, multiple cured polymers can be disposed on the inner mold.

In a step 34, uncured molding material is added to an outer mold. The outer mold may be rigid and/or stiff. The outer mold may be formed using 3-D printing. The outer mold may be substantially a similar shape to the shape of flexible sheet 10 that it is desired to form. The outer mold may be substantially a similar shape to the shape of the inner mold and of larger dimensions than the inner mold. The amount of uncured molding material may be selected based on the dimensions of the inner mold, outer mold, and the one or more cured polymers.

In a step 36, the inner mold can be inserted into the outer mold or disposed adjacent to the outer mold such that the uncured molding material is in contact with the cured polymer. This may cause the uncured molding material to substantially cover the one or more cured polymers. A force may be applied to the inner mold relative to the outer mold to ensure that an appropriate position of the inner mold relative to the outer mold is maintained.

In a step 38, the uncured molding material may be cured in contact with the cured polymer to form the flexible sheet 10. The curing may be performed such that the cured polymer comprising the hollow chamber 18 and the embedded tube 20 is integral to the formed flexible sheet 10.

In a step 40, the inner mold and the outer mold may be removed from the flexible sheet 10. The flexible sheet may substantially maintain the shape of the inner mold and/or the outer mold.

The method described above may include curing an uncured polymer in contact with an already-cured polymer in order to form a complex cured object, such as the flexible sheet 10. This flexible sheet can comprise hollow chambers 18 and embedded tubes 20. In some examples, the polymer may comprise an elastomer. In some examples, the polymer may comprise silicone.

Accordingly, an improved flexible sheet with a hollow chamber has been disclosed, as well as an improved method of control.

It should be understood by those skilled in the art that while the present invention has been described with reference to exemplary embodiments, it is not limited to the disclosed exemplary embodiments. Various modifications, combinations, sub-combinations and alterations may occur depending on design the requirements and other factors insofar as they are within the scope of appended claims or the equivalents thereof. Features from any example or embodiment of the present disclosure can be combined with features from any other example or embodiment of the present disclosure.

The invention claimed is:

1. An apparatus comprising:
a flexible sheet having a hollow chamber disposed within a thickness of the flexible sheet at a localised region of the flexible sheet, and an opening for transfer of a fluid between an exterior of the flexible sheet and the hollow chamber;
a fluid source configured to supply a fluid to the hollow chamber via the opening to cause an increase in at least one of the surface area or the volume of the flexible sheet at the localised region; and
a control circuit for controlling the fluid source, the control circuit configured to identify a category of movement of a user as movement of the user is occurring, to predict a required change in pressure in the hollow chamber responsive to the identified category of movement and responsive to previously logged data associated with previous control actions carried out by the control circuit in controlling the fluid source, and to pre-emptively adjust the supply of fluid to or from the hollow chamber responsive to the predicted required change in pressure, wherein the fluid is a gas, and the fluid source comprises a compressed gas canister configured to dispense the gas, wherein the control circuit comprises at least one electronic sensor, wherein the control circuit is further configured to pre-emptively adjust the fluid based on current feedback from the at least one sensor and independently of an input command from the user, wherein the logged data comprises previous feedback supplied by the at least one sensor during the previous control operations, the logged data stored in a memory of the control circuit.

2. The apparatus of claim 1, wherein the control circuit uses machine learning techniques upon the logged data to pre-emptively adjust the supply of fluid.

3. The apparatus of claim 1, wherein the logged data further comprises timing data associated with a detected regular pattern of use by the user.

4. The apparatus of claim 1, wherein the logged data further comprises geopositioning data associated with a detected regular pattern of use by the user.

5. The apparatus of claim 1, wherein the control circuit is further configured to receive an override command from a user and, in response, disable the pre-emptive adjustment of the supply of fluid, the control circuit further configured to subsequently incorporate the receipt of the override command into the logged data for future use by the control circuit in pre-emptive adjusting the supply of fluid at a later date.

6. The apparatus of claim 1, further comprising the control circuit being configured to interrupt or reverse the pre-emptive adjustment of the supply of fluid in response to a user input to cancel the adjustment of the supply of fluid.

7. The apparatus of claim 1, wherein the gas is controllably circulated to apply a cooling effect upon the flexible sheet.

8. The apparatus of claim 1, wherein the gas is carbon dioxide.

9. The apparatus of claim 8, further comprising at least a selected one of:
the compressed fluid source is replaceable or refillable; or
the control circuit is configured to control the supply of fluid to the hollow chamber by releasing the gas from the compressed fluid source into the hollow chamber and/or to control the supply of fluid from the hollow chamber by releasing gas to the exterior of the hollow chamber and optionally to the exterior of the apparatus.

10. The apparatus of claim 1, wherein the apparatus is one of a prosthetic limb, or a medical or non-medical device arranged for skin contact.

11. A system comprising the apparatus of claim 1 and a remote device in communication with the control circuit of the apparatus, wherein the remote device is configured to analyse the previous feedback from the at least one sensor and/or the past control operations, to determine periodic patterns indicative of the category of movement and/or characteristic patterns or sequences of control, and to transmit data regarding the periodic patterns indicative of the category of movement and/or characteristic patterns or sequences of control to the apparatus.

* * * * *